(12) United States Patent
Sowelam et al.

(10) Patent No.: US 7,896,813 B2
(45) Date of Patent: Mar. 1, 2011

(54) SYSTEM AND METHOD FOR MONITORING PERIODIC BREATHING ASSOCIATED WITH HEART FAILURE

(75) Inventors: Sameh Sowelam, Maple Grove, MN (US); H. Toby Markowitz, Roseville, MN (US); Mark K. Erickson, Brooklyn Park, MN (US); Ioana Nicolaescu, Anchorage, AK (US)

(73) Assignee: Medtronic, Inc., Minneapolis, MN (US)

(*) Notice: Subject to any disclaimer, the term of this patent is extended or adjusted under 35 U.S.C. 154(b) by 735 days.

(21) Appl. No.: 11/278,187

(22) Filed: Mar. 31, 2006

(65) Prior Publication Data

US 2007/0239055 A1 Oct. 11, 2007

(51) Int. Cl.
*A61B 5/08* (2006.01)
(52) U.S. Cl. .................................. 600/529; 600/484
(58) Field of Classification Search .............. 600/483, 600/484, 529–543
See application file for complete search history.

(56) References Cited

U.S. PATENT DOCUMENTS

| | | | |
|---|---|---|---|
| 4,702,253 A | 10/1987 | Nappholz et al. | |
| 5,271,395 A | 12/1993 | Wahlstrand et al. | |
| 5,385,144 A * | 1/1995 | Yamanishi et al. | 600/330 |
| 6,168,568 B1 * | 1/2001 | Gavriely | 600/529 |
| 6,454,719 B1 * | 9/2002 | Greenhut | 600/484 |
| 6,589,188 B1 | 7/2003 | Street et al. | |
| 6,731,984 B2 | 5/2004 | Cho et al. | |
| 6,856,829 B2 | 2/2005 | Ohsaki et al. | |
| 7,070,568 B1 * | 7/2006 | Koh | 600/508 |
| 7,094,207 B1 * | 8/2006 | Koh | 600/529 |
| 2002/0029000 A1 | 3/2002 | Ohsaki et al. | |
| 2003/0195571 A1 | 10/2003 | Burnes et al. | |
| 2004/0134496 A1 | 7/2004 | Cho et al. | |
| 2004/0138719 A1 * | 7/2004 | Cho et al. | 607/42 |
| 2004/0210261 A1 * | 10/2004 | King et al. | 607/9 |
| 2007/0118054 A1 * | 5/2007 | Pinhas et al. | 600/587 |
| 2007/0167843 A1 * | 7/2007 | Cho et al. | 600/484 |
| 2007/0239057 A1 * | 10/2007 | Pu et al. | 600/529 |
| 2008/0183083 A1 * | 7/2008 | Markowitz et al. | 600/484 |

FOREIGN PATENT DOCUMENTS

WO 2005018737 3/2005

OTHER PUBLICATIONS

PCT International Search Report, PCT/US2007/063536.

* cited by examiner

*Primary Examiner* — Patricia C Mallari
*Assistant Examiner* — Karen E Toth
(74) *Attorney, Agent, or Firm* — Stephen W. Bauer; Reed A. Duthler

(57) ABSTRACT

A system and method for monitoring in a patient includes producing sensor signals representative of a physiologic parameter associated with respiration. A periodic breathing cycle is detected based on the sensor signals. An output is produced as a function of the cycle length.

13 Claims, 5 Drawing Sheets

SYSTEM AND METHOD FOR MONITORING PERIODIC BREATHING ASSOCIATED WITH HEART FAILURE

BACKGROUND OF THE INVENTION

The present invention relates generally to implantable and external devices for monitoring physiologic parameters associated with respiration. In particular, the present invention relates to monitoring periodic breathing, such as central sleep apnea, as an indicator or biomarker of congestive heart failure.

Sleep apnea is generally defined as a cessation of breathing during sleep, and can typically be categorized as one of two basic types: central sleep apnea (CSA) or obstructive sleep apnea (OSA). OSA is the more common type of sleep apnea, and is generally characterized by repetitive pauses in breathing during sleep due to the obstruction and/or collapse of the upper airway. CSA is an apnea that is neurally mediated. The apnea is caused by neural signaling (or lack thereof) causing cessation of substantially all respiratory effort during sleep, usually accompanied with decreases in blood oxygen saturation ($SaO_2$).

Unlike OSA, CSA does not necessarily involve blockage of an airway. Instead, CSA involves failure of the brain to send appropriate signals to initiate action of the muscles required for respiration. CSA occurs during sleep when an acute increase in ventilation results in a decrease in the level of carbon dioxide in a patient's bloodstream (i.e., the $PaCO_2$). When the $PaCO_2$ falls below a threshold level required to stimulate breathing, the "central" (as in Central Nervous System) drive to respiratory muscles and airflow ceases, initiating central apnea. This apnea persists until the patient's $PaCO_2$ level rises above the threshold required to stimulate ventilation, upon which the cycle of hyperpnea followed by apnea may repeat. This is referred to as "periodic breathing".

Patients with congestive heart failure (CHF) frequently suffer from CSA as well as similar periodic breathing disorders such as Cheyne-Stokes breathing while asleep or awake. The presence of CSA is a reflection of a compromised cardiac function, with CSA being recognized as a consequence of CHF. See Floras et al., *Circulation,* 107(2003): 1822-1826. As such, the presence, or worsening in the severity, of periodic breathing may alert a healthcare provider to the necessity of intensifying a patient's CHF therapy.

BRIEF SUMMARY OF THE INVENTION

A method and a device for monitoring periodic breathing in a patient produces signals representative of a physiologic parameter associated with respiration. A periodic breathing cycle is detected based on the sensor signals and a cycle length is computed. An output representing a biomarker of Congestive Heart Failure status is produced as a function of the cycle length. The output biomarker may be useful to healthcare providers for various purposes such as, for example, diagnosing periodic breathing or CHF, tracking progression of periodic breathing or CHF, and/or treating periodic breathing or CHF.

DETAILED DESCRIPTION

Figure 1:
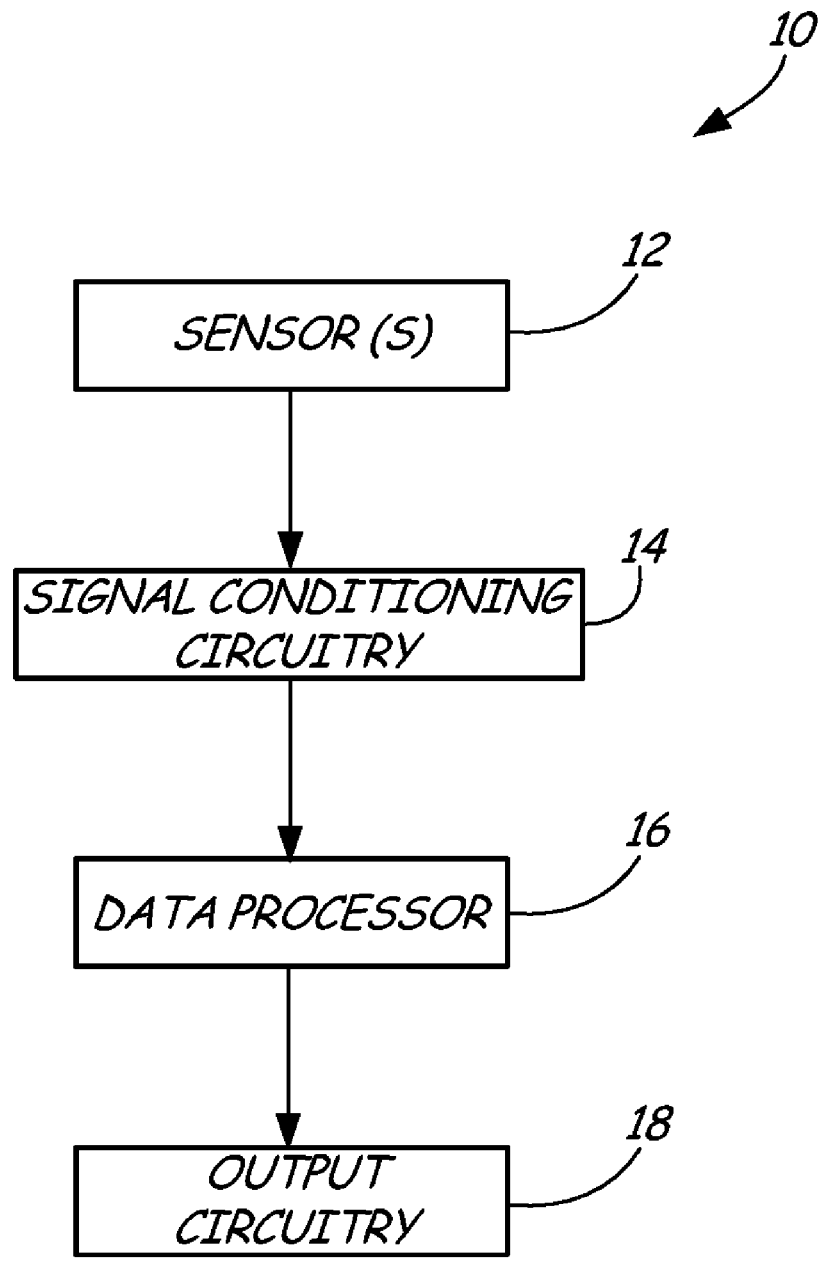
FIG. 1 shows a block diagram of a device of the present invention for monitoring periodic breathing.

FIG. 1 shows a block diagram representation of a monitoring device of the present invention for detecting and monitoring periodic breathing. As shown in FIG. 1, periodic breathing monitor 10 includes one or more sensors 12, signal conditioning circuitry 14, data processor 16, and output circuitry 18. Sensor(s) 12 produce sensor signals representative of one or more physiologic parameters associated with respiration of a patient. Sensor(s) 12 are in communication with signal conditioning circuitry 14, which conditions sensor signals received from sensor(s) 12 for transmittal to data processor 16. Data processor 16 monitors the conditioned sensor signals and produces a biomarker output as a function of the condition sensor signals. The biomarker output may be stored and/or communicated to output circuitry 18 for transmittal to a remote location for further processing, storage, and/or communication to a healthcare provider or patient.

Monitor 10 may be an implantable device configured for implantation within a patient, an external device configured to be worn by the patient, or may include both implantable and external components linked by telemetry. For purposes of patient compliance, it may be preferable to have monitor 10 be an implantable device. Monitor 10 may be capable of collecting data other than data useful for diagnosing and treating sleep apnea and may also deliver therapy to the patient. For example, in some embodiments, monitor 10 may be implemented in a pacemaker, an implantable cardioverter defibrillator (ICD), or a cardiac resynchronization therapy (CRT) device.

Monitor 10 may include any number of sensors 12 capable of detecting one or more physiologic parameters associated with respiration and producing a sensor signal representative of the physiologic parameter(s). In some embodiments, monitor 10 may include one or more inputs for communicating with one or more sensors 12 spatially removed from monitor 10. It may include one or more inputs for receiving sensor signals from one or more implanted and/or external sensor(s) 12, either through electrical leads or by telemetry Sensor(s) 12 may be any type of sensor known in the art that are useful for sensing physiologic parameters associated with respiration. Sensor(s) 12 may be implantable sensors, external sensors for use outside a patient's body, or a combination of both. Examples of suitable sensors 12 for detecting physiologic parameters associated with respiration include oxygen level sensors (e.g., finger-tip oxygen sensors), pulse oximeter sensors, peripheral arterial tonometry sensors, carbon dioxide level sensors, impedance sensors for detecting minute ventilation (MV), pressure sensors for monitoring blood pressure or sensing airflow (breathing), microphones for monitoring breath sounds, mechanical or temperature sensors for monitoring airflow (breathing) or chest movement, thoracic effort sensors (e.g., respiratory belts worn around the chest), abdominal effort sensors (e.g., respiratory belts worn around the abdomen), any other sensor capable of monitoring a parameter indicative or predictive of the occurrence of apnea and/or hyperpnea, and any combination of these. In some embodiments, sensor 12 may be an intracardiac sensor capable of measuring impedance between atrial and ventricular electrodes or an intrathoracic impedance sensor that measures impedance across the thorax. Sensor(s) 12 may also provide signals that allow monitor 10 to distinguish between inspiration and exhalation.

Monitor 10 may include one or more sensor(s) 12 capable of detecting one or more parameters useful in determining whether the patient is asleep or awake. Inclusion of such sleep detection sensor(s) may allow monitor 10 to conserve power by, for example, only performing certain types of processing activities after the patient has been determined to be asleep. Examples of sensors 12 useful in sleep detection include position sensors, activity sensors (e.g., piezoelectric crystals or accelerometers), and combinations of these. Various devices are available for sensing position and/or activity. For example, position sensors have been used to determine certain cardiac pacing regimes in heart failure patients and activity sensors have been used for rate-responsive pacing. In some embodiments, whether the patient is asleep may be determined based on historic respiration data such as, for example, stored data pertaining to MV, $SaO_2$ levels, $PaCO_2$ levels, breathing rates, etc. Monitor 10 can also be used to detect and monitor periodic breathing while the patient is awake.

Any type of output or communication circuitry known in the art may be implemented for output circuitry 18. The configuration of output circuitry 18 may vary depending on whether monitor 10 is intended for implantation or external use. In some embodiments, output circuitry 18 may comprise telemetry circuitry for communicating with a remote system.

Figure 2:
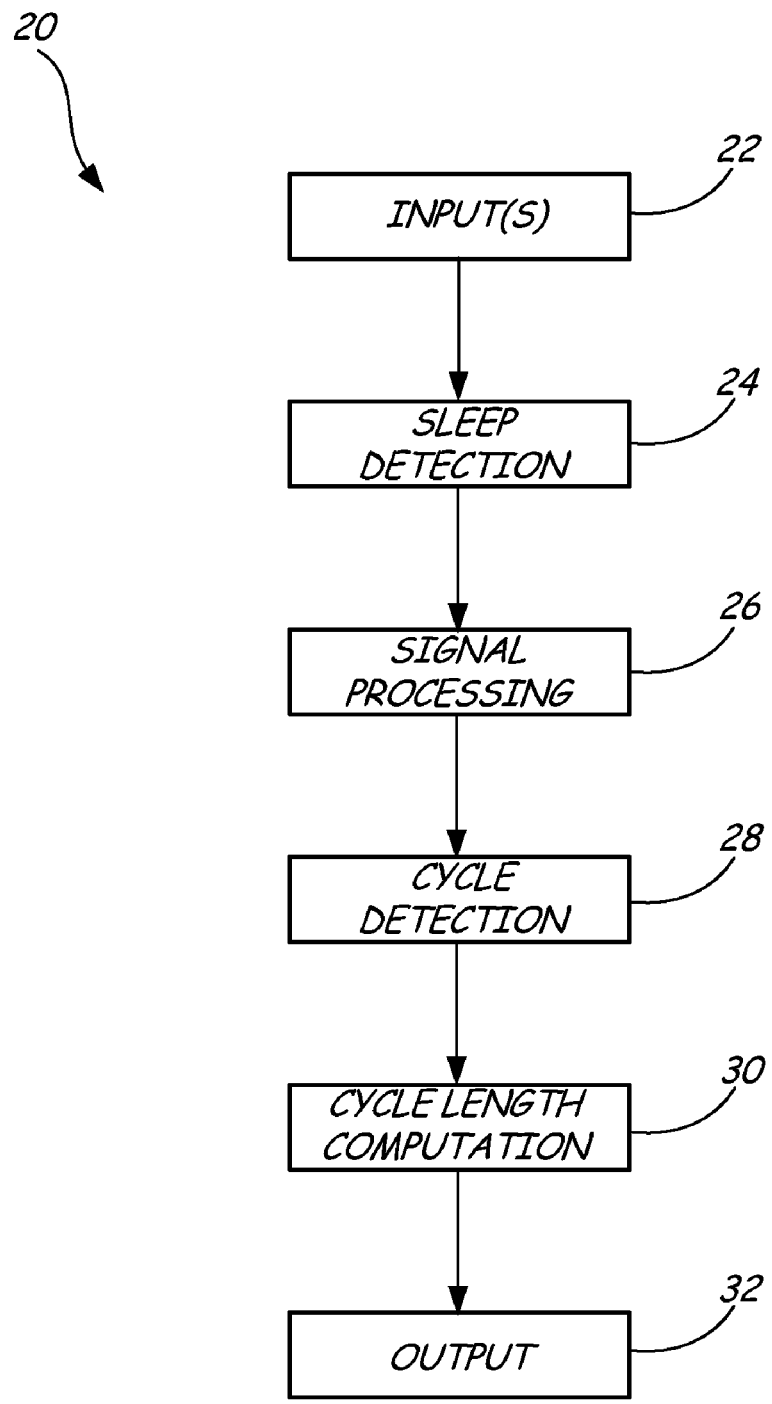
FIG. 2 shows a flow diagram of a method for producing an output.

FIG. 2 shows method 20 performed by monitor 10 for monitoring CSA of a patient and producing a CSA output. As shown in FIG. 2, one or more physiologic parameters associated with respiration are sensed by sensor(s) 12, and sensor signals representative of the physiologic parameter(s) are input to monitor 10 (step 22). If the monitored patient is determined to be asleep (step 24), the sensor signals are conditioned by signal conditioning circuitry 14 (step 26), and the conditioned signals are communicated to data processor 16. The signal processing may include, for example, analog-to-digital conversions, time-interval conversions, noise filtering, etc. In some embodiments, sleep detection may occur at a different point in method 20 than shown in FIG. 2 (e.g., after signal conditioning or another downstream step) or not at all.

After receiving the conditioned sensor signals, data processor 16 processes the conditioned sensor signals to detect occurrence of periodic breathing cycles (PBCs) (step 28). Techniques for detecting PBCs are discussed in further detail below in relation to FIG. 6. Cycle length CL for each detected PBC is then computed (step 30) and a biomarker output (in this case a CSA output) is produced as a function of cycle length CL (step 32). The CSA output may be stored and/or transmitted to a remote system for communicating to a healthcare provider or the patient.

The cycle lengths for PBCs attributable to CSA are inversely proportional to cardiac output. As such, an increase in cycle length is indicative of a decrease in cardiac output, which may indicate a progression in CHF disease state. Thus, relative changes in cycle length CL over time may be particularly useful in monitoring the progression of CHF in a patient. This information may be included or summarized in the biomarker outputs.

The CSA output may contain any CSA-related information extracted from cycle length data that may be useful to a healthcare provider in identifying, monitoring, and/or treating either CSA or CHF. In some embodiments, the CSA output may be a numeric output related to CSA. Examples of such numeric CSA outputs include numeric values corresponding to cycle length CL, ranges of sensed cycle lengths CL, and statistical measures related to cycle length CL. Examples of statistical measures related to cycle length CL include standard deviations for cycle length CL, mean values for cycle length CL, median values for cycle length CL, rates of change for cycle length CL, and sample variances for cycle length CL. In addition, the output may also report percent time in CSA, and CSA episode durations.

The CSA output may include a diagnosis or treatment recommendation for a healthcare provider, an indication of a CSA-related disease state or progression, or information related to CSA or CHF trends. The CSA output may provide a treatment recommendation that a patient undergo cardiac resynchronization therapy (CRT) if occurrence of CSA has been detected, the patient has the appropriate indications, and the patient has not undergone CRT. In some embodiments, if method 20 determines that the patient is suffering from OSA, the CSA output may include a recommendation that the patient undergo a sleep study with the possibility that continuous positive airway pressure (CPAP) therapy may be indicated and prescribed.

Preferably, the CSA output is a validated CSA output that has been filtered to remove, or reduce the influence of, false positives such as, for example, OSA. Techniques for producing validated CSA outputs are discussed in further detail below in conjunction with FIG. 5.

Another potential source of false positives is hypopnea, which is abnormally shallow breathing. Monitor 10 may, for example, use signal amplitude measurements to distinguish hypopnea from periodic breathing such as CSA.

Figure 3:
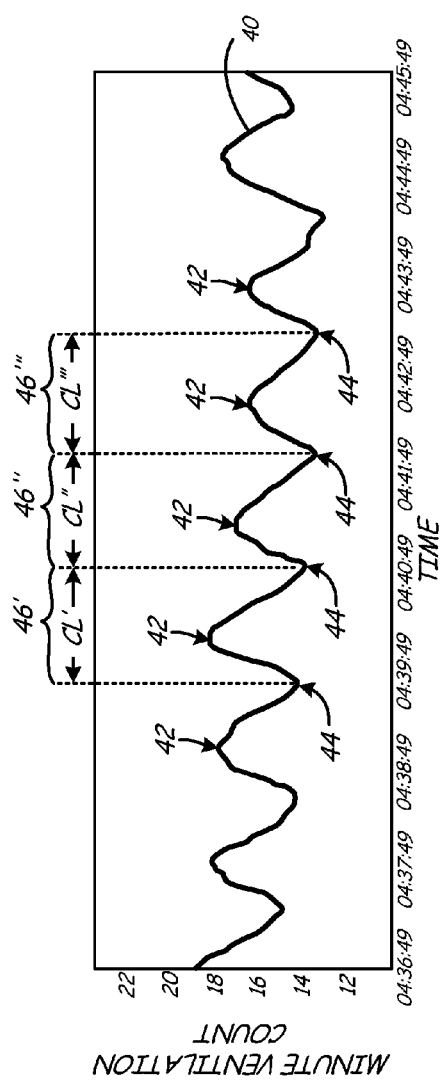
FIG. 3 shows a plot of periodic breathing clusters measured by minute ventilation and indicative of CSA.
Figure 4:
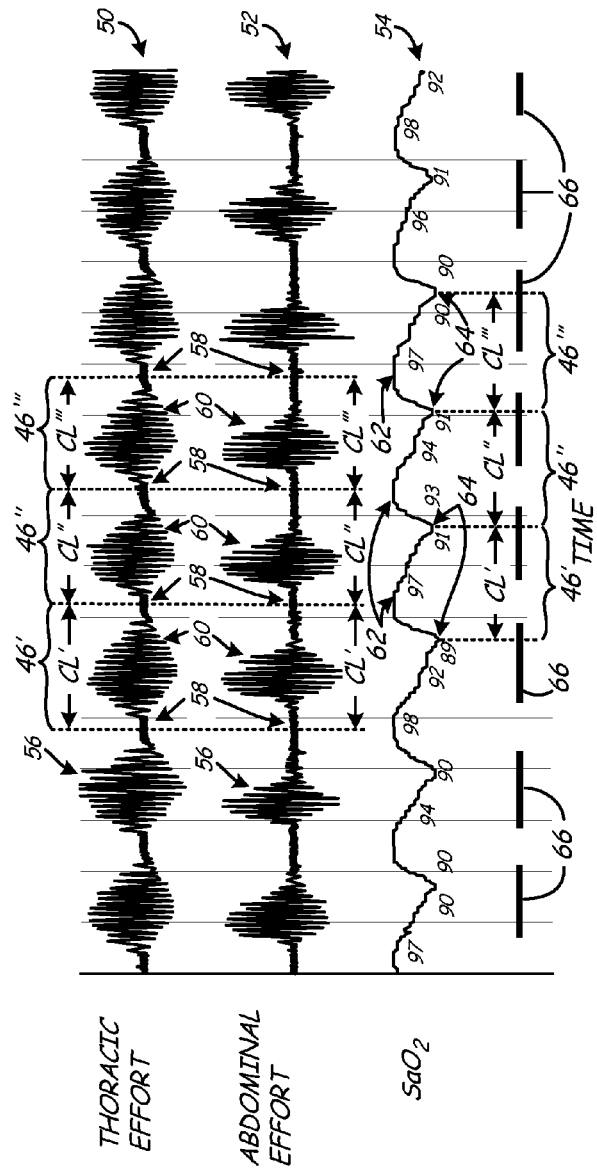
FIG. 4 shows a plot of periodic breathing clusters indicative of CSA as measured by thoracic effort, abdominal effort, and oxygen saturation, respectively.

FIGS. 3 and 4 are plots of physiologic data associated with respiration that exhibit PBC clusters indicative of CSA. The present invention may utilize such PBC clusters to detect and monitor CSA.

FIG. 3 shows MV data that includes clusters of PBCs indicative of CSA. MV is representative of a volume of air inspired or expired per unit time and is typically given in liters of air per minute. MV may be defined by the equation:

$$MV = RR \times VT,$$

where RR is a respiration rate in breaths per minute and VT is a tidal volume of each inspired or expired breath in liters.

FIG. 3 shows MV plot 40, which is a plot of MV versus time during a CSA episode, with the level of MV indicated in MV counts. (For further discussion of MV counts see U.S. Pat. No. 6,731,984). The level of MV at a particular point in time is represented as a point on MV plot 40. MV plot 40 includes peaks 42 and troughs 44 corresponding to PBCs 46. Troughs 44 coincide with periods of apnea associated with CSA and peaks 42 correspond with periods of hyperpnea associated with CSA.

Each PBC 46 attributable to CSA has a cycle length CL. The values of successive cycle length CL'-CL''' corresponding to successive PBCs 46'-46''' may differ. However, cycle lengths stemming from CSA are generally much more consistent than those stemming from OSA due to the nature of the physiologic conditions associated with OSA and CSA. Thus, for example, as shown in FIG. 3, successive cycle lengths CL'-CL''' may each have substantially the same value or may fall within a relatively narrow range of values that, in most embodiments, will be narrower than a representative range of cycle length values attributable to OSA. Some embodiments of the present invention utilize this increased consistency in cycle length CL for CSA (relative to OSA) to filter out PBCs attributable to OSA.

Cycle length CL may be defined using various conventions, which will generally yield the same cycle length value for a given PBC if the starting and ending points for the cycle are defined consistently. For example, cycle length CL may be defined to be the distance (in time) between adjacent peaks 42, the distance (in time) between adjacent troughs 44, or the distance (in time) between any other two points on MV plot 40 belonging to adjacent PBCs 46 (e.g., PBC 46' and 46" or PBC 46" and 46''') and corresponding to a consistent point in each respective cycle.

Methods for determining MV indirectly using implantable devices such as pacemakers are well known in the art. (See, for example, U.S. Pat. No. 5,271,395). For example, MV may be determined indirectly by measuring impedance changes in the thoracic cavity between two or more cardiac electrodes (e.g., electrodes used for pacing and/or sensing in connection with cardiac pacemakers). It is well known that a change in thoracic impedance corresponds to a change in VT (tidal volume), and a frequency of such changes over time corresponds to RR (respiration rate). (See, for example, U.S. Pat. No. 4,702,253).

FIG. 4 illustrates physiologic parameter data including clusters of PBCs detected using a thoracic effort sensor, an abdominal effort sensor, and a fingertip oxygen sensor for measuring $SaO_2$, respectively. FIG. 4 includes thoracic effort plot 50, abdominal effort plot 52, and $SaO_2$ plot 54 corresponding to a CSA episode. Each of plots 50-54 includes clusters of PBCs 46 exhibiting cycle lengths CL attributable to CSA, with each spike 56 indicating an individual breath. Thoracic effort plot 50 and abdominal effort plot 52 include PBCs 46 with apneas 58 alternating with hyperpneas 60. For plots 50 and 52, cycle lengths CL corresponds graphically to the distance (in time) for each PBCs 46 as measured from the midpoints of adjacent apneas 58.

$SaO_2$ plot 54 illustrates graphically how cycle lengths CL may be extracted from blood oxygen data by considering cycles of oxygen saturations and desaturations to identify PBCs 46. Relative to plots 50 and 52, $SaO_2$ plot 54 is shifted later in time (i.e., to the right) due to the time required for blood to travel from the heart and lungs to the fingertip, upon which the oxygen sensor is mounted. $SaO_2$ plot 54 includes peaks 62 and troughs 64, with troughs 64 coinciding with oxygen desaturations 66. Periods of oxygen saturation occur between adjacent desaturations 66. Cycle length CL, as shown in FIG. 4, corresponds graphically to the distance (in time) between adjacent troughs 64.

Monitor 10 may utilize data such as that included in FIGS. 3 and 4 to determine cycle lengths CL using data analysis techniques that are well known in the art, including, for example, zero-crossing techniques. In some embodiments, monitor 10 may consider two or more sets of data obtained from sensors 12 that either (1) sense different physiologic parameters or (2) utilize different sensing technologies to monitor the same physiologic parameter. Such diversity in sensing technology and/or nature of sensed physiologic parameters may increase the reliability (or validity) of the outputs generated by monitor 10.

Figure 5:
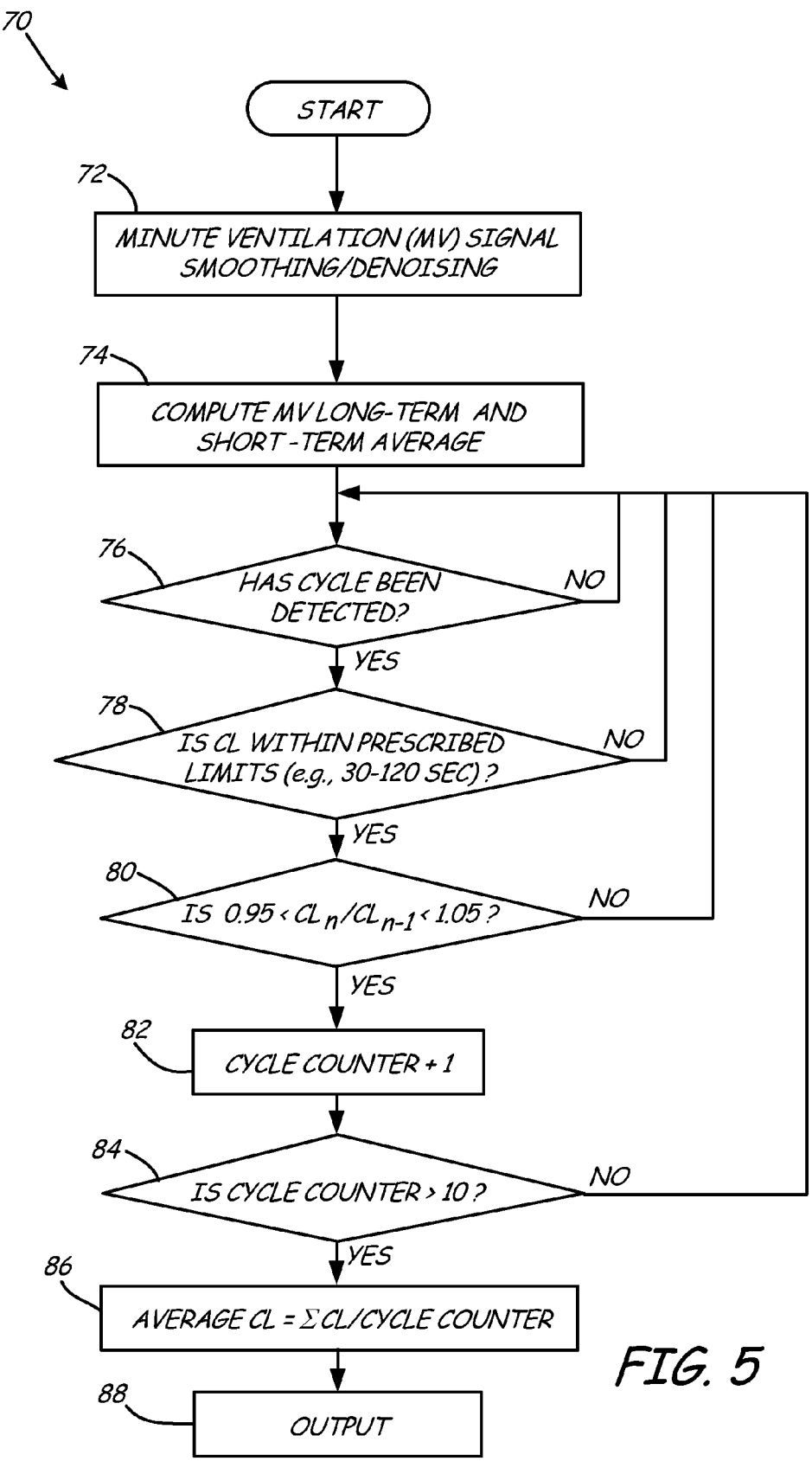
FIG. 5 shows one embodiment of the method of FIG. 2 for producing the output.

FIG. 5 shows method 70, which is one embodiment of method 20 of FIG. 2. Method 70 generates an output as a function of thoracic impedance data representative of MV. Monitor 10 inputs sensor signals from an MV sensor 12 and conditions the sensor signals using signal smoothing and denoising (step 72). Long-term and short-term MV averages are computed (step 74) based on the conditioned sensor signals. Data processor 16 analyzes the long-term and short-term MV averages to detect occurrence of a PBC (step 76) (which is discussed in further detail below in the discussion of FIG. 6). If occurrence of a PBC is detected, data processor 16 computes cycle length CL corresponding to the PBC and determines whether cycle length CL falls within a prescribed range. As shown in the embodiment of FIG. 5, the prescribed range for cycle length CL is set between about 30 seconds and about 120 seconds (step 78). The limits of the prescribed range may be set to screen out false positives such as, for example, OSA.

If the cycle length CL is within the prescribed range, then data processor 16 determines whether cycle length of the detected PBC is within a specified proximity of a reference cycle length (step 80). As shown in FIG. 5, the reference cycle length is a cycle length $CL_{n-1}$ of a preceding PBC. To proceed to step 82, cycle length CL must be within about 5% of cycle length $CL_{n-1}$. In other embodiments, the reference cycle length and/or the proscribed proximity of step 80 may be any suitable values sufficient to screen out false positives such as OSA. If cycle length CL is within a specified proximity of the reference cycle length, this causes a value of a cycle counter to increment by one (step 82). If the cycle length is not within the specified proximity of the reference cycle length, then method 70 returns to step 76. This process continues until the cycle counter reaches a count of 10 or more (step 84), at which point an average cycle length CL is computed for cycle length CL (step 86). The output is computed as a function of average cycle length CL (step 88). The output is then communicated to the healthcare provider or patient or stored for later communication to a healthcare provider and/or patient.

The average cycle length CL produced by step 88 is a validated cycle length that has been validated due to inclusion of steps 78-84, which detect and filter some, if not all, PBCs occurring as a result of OSA. As discussed above, OSA is typically associated with a less consistent PBC pattern than CSA and, in most instances, will be filtered out via steps 78-84. In some embodiments, the lengthening of average cycle length CL (since it indicates a reduction in cardiac output) beyond a diagnostic threshold may be an indicator of worsening prognosis of CHF, which may cause monitor 10 to communicate a suitable output to a healthcare provider.

The stringency of steps 78-84 may be adjusted higher or lower to strike a desired balance between periodic breathing detection and OSA filtering. To accomplish this, the ranges of steps 80, 82, and/or 84 may be increased or decreased to provide a desired degree of filtering/validation. Likewise, filtering steps may be added or removed from method 70.

Figure 6:
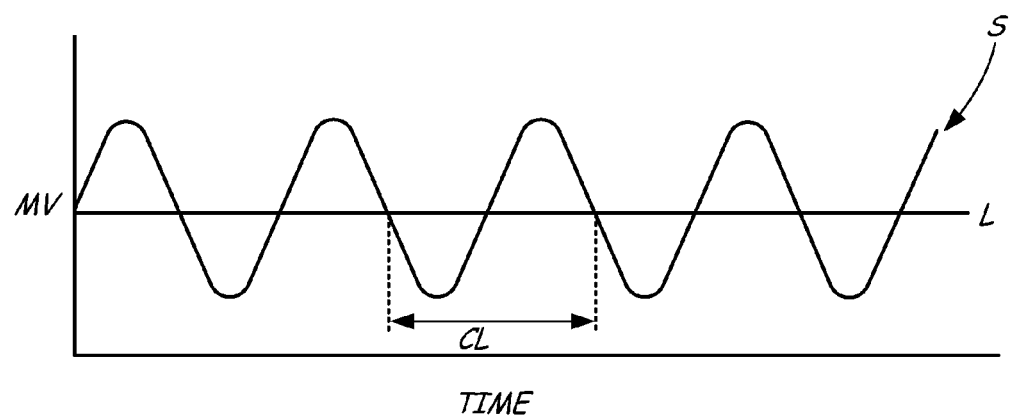
FIG. 6 shows a comparison of long-term average minute ventilation and short-term average minute ventilation for use in computing the output of FIG. 5.

FIG. 6 shows a plot of average short-term MV versus average long-term MV and illustrates how a comparison of the two may be utilized to determine cycle length CL. As shown in FIG. 6, cycle length CL corresponds to the distance (in time) between two consecutive intersection points of plot S (which is a plot of short-term MV average over time) and plot L (which is a plot of long-term MV average over time). A zero-cross methodology or any other suitable data analysis technique known in the art may also be employed by monitor 10 to determine cycle length CL.

Techniques similar to those employed in conjunction with method 70, or any other suitable techniques known in the art, may be employed to determine cycle length CL as a function of other physiologic parameters detected by sensor(s) 12.

Thus, as described above, the present invention includes a system and method for monitoring physiologic parameters associated with respiration and detecting periodic breathing patterns indicative of CSA and CHF. Clusters of periodic breathing cycles are detected and a CSA output is produced as a function of a cycle length associated with the periodic breathing cycles. The output is preferably an output that has been validated to filter out false positives such as, for example, periodic breathing patterns attributable to OSA and hypopneas.

Although the present invention has been described with reference to preferred embodiments, workers skilled in the art will recognize that changes may be made in form and detail without departing from the spirit and scope of the invention.

The invention claimed is:

1. A device for monitoring a patient, the device comprising:
   an input for receiving sensor signals representative of one or more physiologic parameters associated with respiration;
   signal conditioning circuitry in communication with the input to condition the sensor signals; and
   a data processor in communication with the signal conditioning circuitry, the data processor programmed to;
   receive the conditioned sensor signals and detect breathing cycles as a function of the conditioned sensor signals, a breathing cycle comprising a cycle of hyperpnea followed by apnea;
   determine cycle lengths of the detected breathing cycles;
   determine regularity of the cycle lengths; and
   determine whether the breathing cycles are indicative of central sleep apnea based upon the determined regularity of the cycle lengths.

2. The device of claim 1, and further comprising:
   communication circuitry in communication with the data processor to communicate the output to a remote system.

3. The device of claim 1, and further comprising:
   one or more sensors for detecting the one or more physiologic parameters associated with respiration and producing the sensor signals representative of the physiologic parameters.

4. The device of claim 3, wherein the device includes a plurality of sensors capable of sensing different physiologic parameters associated with respiration and the data processor is further programmed to validate the presence of central sleep apnea as a function of sensor signals generated by the plurality of sensors.

5. The device of claim 1 wherein the data processor is programmed to determine whether the breathing cycle lengths are within a specified proximity of one or more reference cycle lengths.

6. A method for monitoring progression of heart failure in a patient using an implanted device, the method comprising:
   monitoring sensor signals representative of a physiologic parameter associated with respiration using the implanted device;
   detecting breathing cycles based on the sensor signals using the implanted device, a breathing cycle comprising a cycle of hyperpnea followed by apnea;
   determining cycle lengths as a function of the breathing cycles using the implanted device;
   determining regularity of the cycle lengths; and
   producing an output associated with a heart disease state of the patient using the implanted device as a function of the determined regularity of the cycle lengths.

7. The method of claim 6, and further comprising:
   communicating the output to a remote system.

8. The method of claim 6, and further comprising:
   comparing the cycle lengths to a historical cycle length.

9. The method of claim 8, and further comprising:
   communicating the output to a healthcare provider if the cycle lengths exceed the historical cycle length by a specified amount.

10. The method of claim 6, wherein the sensor signals are produced by one or more sensors located outside the patient.

11. The method of claim 6, where the sensor signals are produced by one or more implantable sensors.

12. The method of claim 6, and further comprising:
    determining whether the patient is asleep.

13. The method of claim 6, wherein the output comprises a treatment recommendation.

* * * * *